US010111793B1

(12) United States Patent
Falls et al.

(10) Patent No.: US 10,111,793 B1
(45) Date of Patent: Oct. 30, 2018

(54) IV POLE STAND STOP

(71) Applicants: Garner Sharp Falls, Minter, MS (US); Elizabeth Holland Falls, Durham, NC (US)

(72) Inventors: Garner Sharp Falls, Minter, MS (US); Elizabeth Holland Falls, Durham, NC (US)

( * ) Notice: Subject to any disclaimer, the term of this patent is extended or adjusted under 35 U.S.C. 154(b) by 0 days.

(21) Appl. No.: 15/654,011

(22) Filed: Jul. 19, 2017

(51) Int. Cl.
*A61G 7/00* (2006.01)
*A61G 7/05* (2006.01)
*A61M 5/14* (2006.01)

(52) U.S. Cl.
CPC .......... *A61G 7/0503* (2013.01); *A61M 5/1415* (2013.01)

(58) Field of Classification Search
CPC .............................. A61G 7/0503; A61M 5/415
See application file for complete search history.

(56) References Cited

U.S. PATENT DOCUMENTS

| | | | | | |
|---|---|---|---|---|---|
| 2,533,974 | A * | 12/1950 | Szabo | ................. | A24F 19/0092 248/230.7 |
| 3,712,640 | A * | 1/1973 | Shipman | .................. | B62H 1/02 280/301 |
| 4,821,988 | A * | 4/1989 | Jimenez | .................... | A61G 5/10 248/227.3 |
| 4,834,405 | A * | 5/1989 | Dimaio | ..................... | B62H 1/02 211/22 |
| 5,979,269 | A * | 11/1999 | Su-Chen | ................... | B62J 25/00 280/291 |
| 6,648,357 | B2 * | 11/2003 | Hotch | ....................... | B62H 1/02 280/291 |
| 7,097,191 | B2 * | 8/2006 | Griggs | ..................... | B62H 1/02 248/188.9 |
| 9,290,196 | B1 * | 3/2016 | Siegel | ..................... | B62B 5/049 |
| 2013/0228997 | A1 * | 9/2013 | Fukuhara | ................. | A61G 5/10 280/304.1 |

* cited by examiner

*Primary Examiner* — Anita M King
(74) *Attorney, Agent, or Firm* — Sandberg Phoenix & von Gontard PC

(57) ABSTRACT

A stop for an IV pole stand comprising a collar having a central opening for receiving the pole of the IV stand. The front ends of the collar form a split and the front ends of the collar members and are biased closed. The front ends of the collar are shaped to form cam surfaces such that upon front ends of the collar being forcefully pressed against a pole, the cam surfaces force the front ends of the collar open to receive the pole in the central opening. A stop pad is carried on a spring arm cantilevered from the collar such that upon the stop pad being stepped on by a nurse the spring arm will resiliently deflect downwardly and the stop pad will be pressed against the floor to hold the pole stand in place on the floor.

6 Claims, 7 Drawing Sheets

US 10,111,793 B1

IV POLE STAND STOP

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE DISCLOSURE

This disclosure relates to a stop or lock for an IV (intravenous) pole stand that is mounted on wheels so that a nurse or other medical personnel may conveniently and quickly temporarily lock or otherwise hold the IV pole stand in place on the floor and to prevent the IV pole stand from falling over by stepping on a brake pad (or stop pad) so as to free both of the nurse's hands to change an IV bag, to adjust the flow rate of an IV liquid to a patient, to re-program an IV pump or the like supported on the IV pole stand, or to perform other operations involving the IV pole stand.

Typically, an IV pole stand, such as shown in FIG. 1, is used to support one or more IV bags (not shown in FIG. 1) of an IV liquid in an elevated position relative to the patient, where the IV bag is connected to a flexible IV tube and to an IV needle inserted into a patient's vein so that an IV liquid or a medication injected into the IV line may be intravenously administered to the patient. An IV pump may be mounted on the IV pole stand to administer the IV liquid to the patient at a predetermined rate. Oftentimes, it becomes necessary for a nurse to change a nearly empty IV bag for a new one, to inject a medication into the IV line, or to change the programming of the IV pump to administer the IV liquid to the patient at a different rate. Such operations typically require the nurse to use both hands to carry out such operations. However, because the IV pole stand is typically mounted on wheels and because the weight of IV bags or the weight of an IV pump is carried high on the pole stands, such pole stand are thus top heavy. As a result, it is often necessary that the IV pole stand be held by the nurse during such operations to prevent the IV stand from moving on its wheels and/or to prevent the IV pole stand from tipping or otherwise falling over. However, holding the IV pole in such situations is awkward because the nurse must use one hand to hold the IV pole and thus does not have both hands free to perform the desired operations or tasks. Also, because the poles of IV pole stands are used by numerous hospital personnel, the poles of such pole stands are often contaminated with bacteria such that after touching a pole, the hospital personnel should thoroughly was his or her hands before performing various operations including changing an IV bag, adjusting the infusion rate of an IV pump or injecting a medication into the IV line.

Various wheel or caster systems are known that may be used with IV pole stands where one or more of the wheels or casters supporting the IV pole stand may be provided with a foot operated brake that locks one wheel of the pole stand. However, the actuation and de-actuation of such foot operated brakes on one of the wheels and requires the nurse to find the wheel that is equipped with the brake, which takes time, especially since the pole stand may be supported on four or more wheels. Still further, even with the foot operated brake engaged, it still may be necessary for the nurse to hold the IV pole against falling over with one hand while performing the desired operation. It would be convenient if the nurse could engage and disengage a stop without having to actuate or de-actuate a locking device applied to the wheels. Moreover, it would be desirable if the actuation of a stop not only prevented the IV pole stand from moving on its wheels, but would also hold the pole stand from falling over.

It will be recognized by one of ordinary skill in the art that there are differences between IV pole stands because they are made by many different manufacturers, even though they may be of a similar design. For example, the diameter of the IV pole, the design of the base, and the number of wheels may differ significantly. Thus, it would be desirable if an IV pole brake or stop system were commercially available at low cost that could be rapidly installed on IV pole stands of different manufacturers that did not require the use of even simple hand tools to install, that could be rapidly removed from one IV pole stand and installed on another, that needed no modifications to an IV pole stand, that would effectively lock or hold the IV pole stand in place on the floor and would prevent tipping of a top heavy IV pole stand, and that could quickly release the IV pole stand so that it could be moved on its wheels.

SUMMARY OF THE DISCLOSURE

A stop for an IV pole stand is disclosed that has a base mounted on a plurality of wheels and a pole extending vertically from the base. A spring arm is configured to be affixed to the pole and to extend outwardly from the pole and carrying a stop pad such that upon the stop pad being stepped on by a nurse or the like, the spring arm will resiliently deflect downwardly and the stop pad can be pressed against the floor to hold the pole stand in place on the floor and to resist tipping of the pole stand thus freeing both of the nurse's hands to carryout operations on the IV pole stand.

Another embodiment of a stop for an IV pole stand is disclosed that has a base mounted on a plurality of wheels and has a pole extending vertically from the base. The stop comprises an attachment collar having a central opening adapted to receive the pole, and a stop pad carried by a spring arm cantilevered from the collar member such that upon the stop pad being stepped on by a nurse or the like, the spring arm will resiliently deflect downwardly and the stop pad can be pressed against the floor to hold the pole stand in place on the floor and to resist tipping of the pole stand thus freeing both of the nurse's hands to carryout operations on the IV pole stand.

A stop for an IV pole stand is described having a base mounted on a plurality of wheels, and a pole extending vertically from the base, where the stop comprises an attachment collar that has a pair of collar members that form a central opening for receiving the pole. The collar further has a spring for holding the collar members in a closed position generally surrounding the pole when the stop is applied to a pole of an IV stand. The collar members each have a front end and a rear end, where the front ends of the collar members are biased to a closed position such that the collar members substantially encircle the pole. A spring resiliently holds the collar members in their closed position. The front end of each collar member has a cam surface such that upon the front ends of the collar members being forcefully pressed against a pole the cam surfaces force the collar members open such that the pole can pass between the front ends of the collar so the pole is received in the central opening and such that when the pole is received in the central opening the spring resiliently closes the collar members and holds the collar in place on the pole. A stop pad is supported on a spring arm cantilevered from one of the collar members such that upon the stop pad being stepped on by a nurse or the like, the spring arm will resiliently deflect downwardly and the stop pad can be pressed against the floor to hold the pole stand in place on the floor and to resist tipping of the pole stand thus freeing both of the nurse's hands to carryout operations on the IV pole stand.

A method is disclosed for holding an IV pole stand in place on the floor while a nurse or the like performs performing an operation with an IV bag or other equipment supported on the IV pole stand that does not require the nurse to use one hand to hold the IV pole stand while the operation is carried out. The IV pole stand has a base mounted on a plurality of wheels, and a pole extending up from the base. The method comprises affixing a flexible arm extending therefrom and carrying a stop pad on its distal end, and stepping on the stop pad to frictionally engage the floor thereby to hold the IV pole stand in place and to resist tipping of the IV pole stand.

BRIEF DESCRIPTION OF THE DRAWINGS

Corresponding reference characters indicate corresponding parts throughout the several views of the drawings.

DESCRIPTION OF PREFERRED EMBODIMENTS

Figure 1:
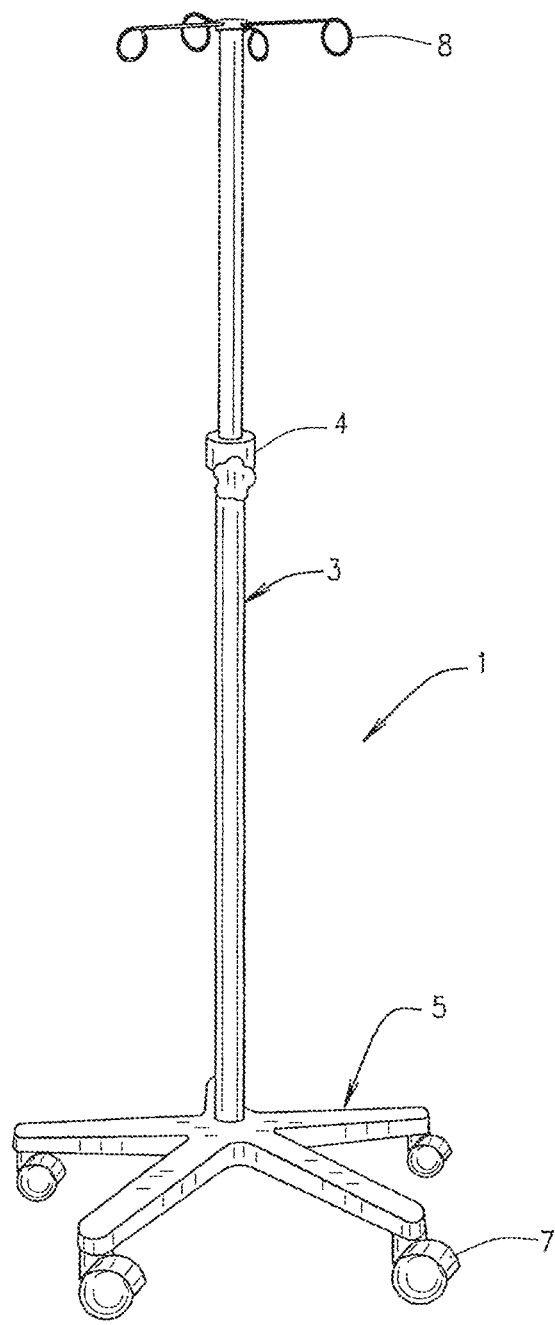
FIG. 1 is a perspective view of a conventional IV pole stand.

Referring now to the drawings, a commercially available IV pole stand is indicated in its entirety at 1. This IV pole stand has a vertical pole 3 mounted on a base 5, which is supported on a plurality of casters or wheels 7 so that the IV pole stand may be readily moved on a floor to be close to a patient lying in a bed, or may be moved along with a patient as the patient is moved in a bed or wheelchair, or as the patient walks around the room or the hospital. Typically, pole 3 has an adjustable clamp 4 (as shown in FIG. 1) so that the height of the pole may be adjusted to a maximum height of about seven feet. The pole 3 is typically provided with hooks 8 or the like at the top of the pole for attaching IV bags (not shown) or the like. As will be appreciated by those skilled in the art, an IV pole stand supporting one or more large IV bags (not shown), where each bag may have a volume of, for example, 3 liters of an IV fluid. The pole 3 may also support other equipment, such as an IV pump (not shown) such that the IV pole stand is top heavy and may have a tendency to fall over or tip while a nurse or other clinician is performing an operation, such as changing an IV bag or re-programming an IV pump supported by the stand. As shown in FIG. 1, IV pole stand 1 may have five or more wheels 7, while as shown in FIGS. 2-4, the IV pole stand has four wheels.

Figure 2:
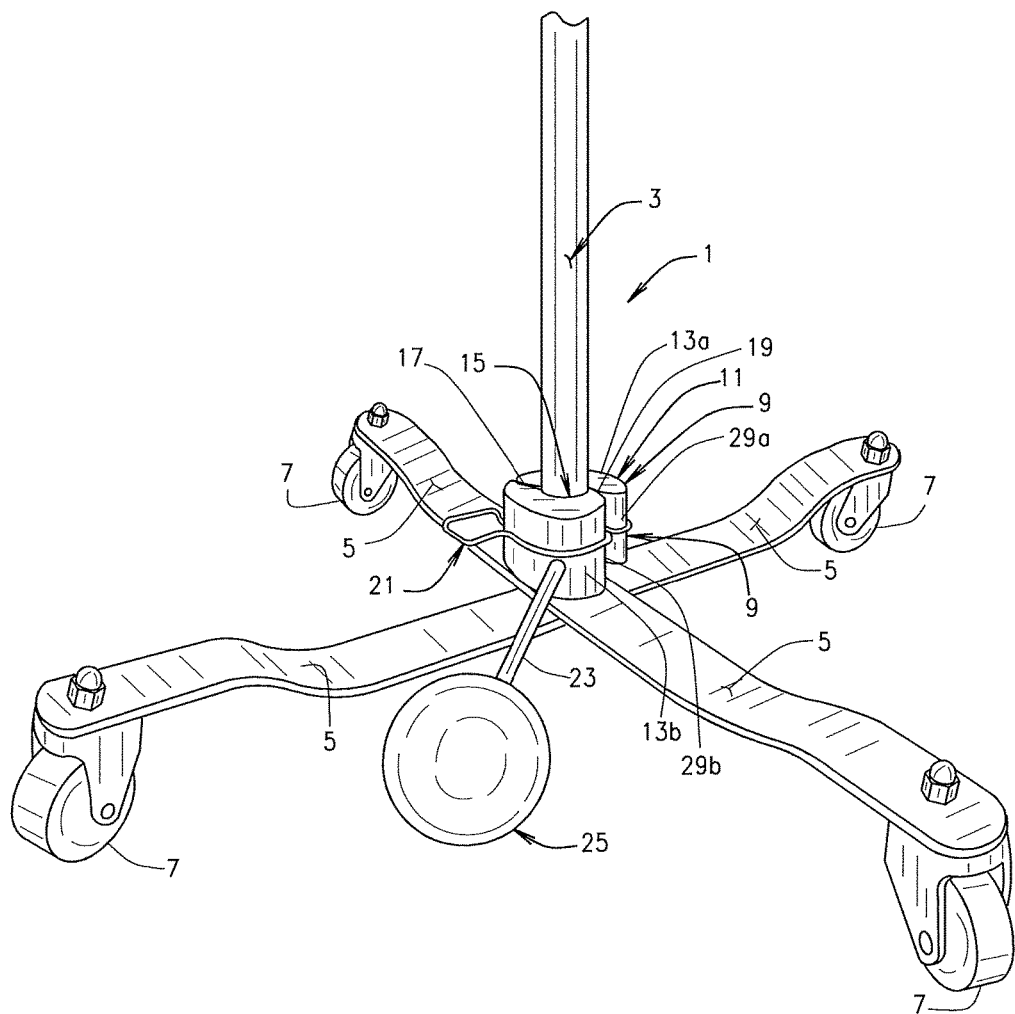
FIG. 2 is a perspective view of the lower portion of a conventional IV pole stand mounted on wheels having an IV pole stop or braking device of the present disclosure mounted thereon.
Figure 3:
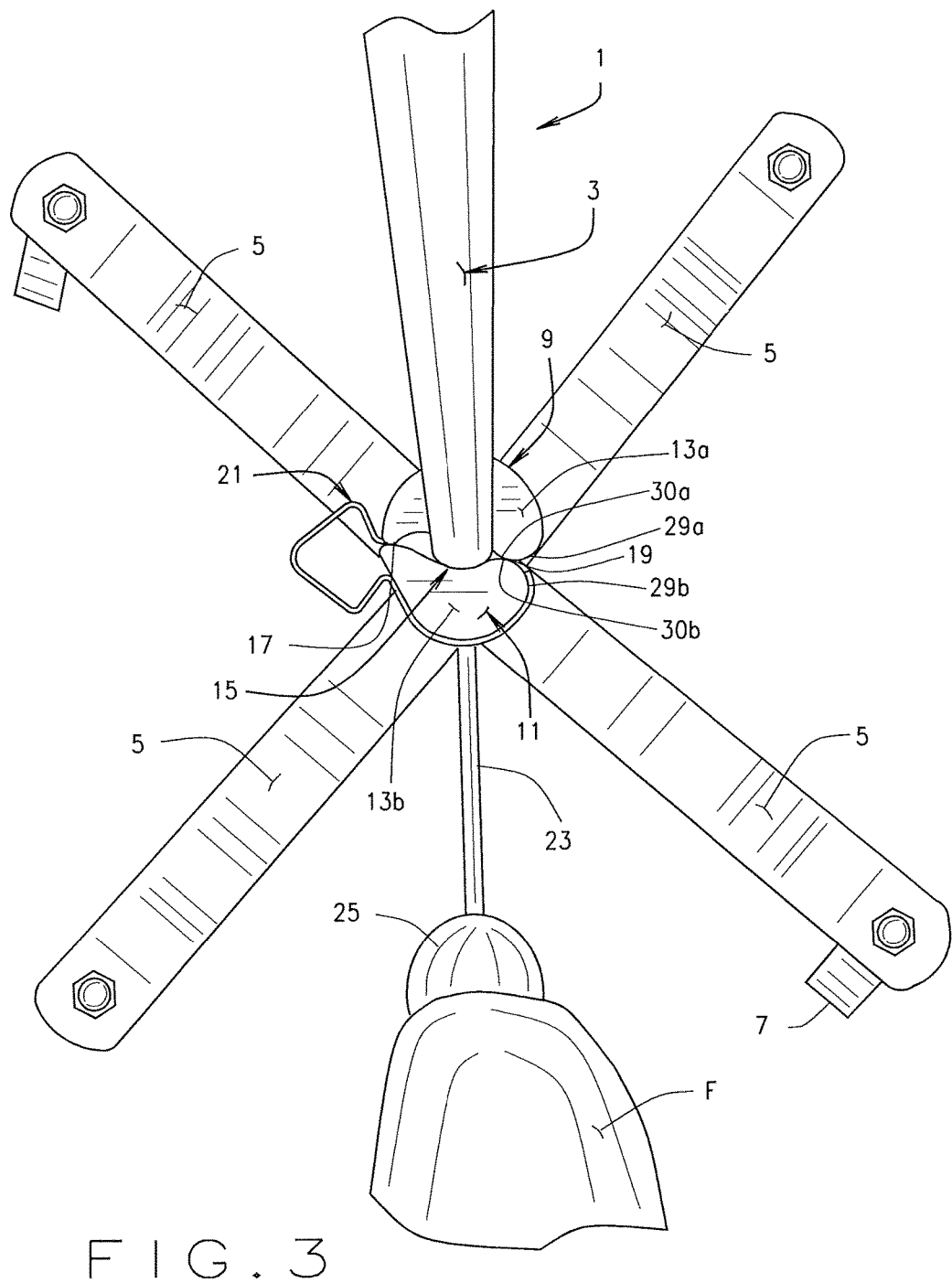
FIG. 3 is a top perspective view of the stop or braking device of the present disclosure has a removable attachment collar is installed around an IV pole stand, illustrating details of a split, openable collar, and illustrating a brake pad or stop pad that may be foot actuated to hold the IV pole stand in place.

An IV pole stand stop or brake device of one preferred embodiment of the present disclosure is indicated in its entirety at 9 and is shown in FIGS. 2-3 to comprise a split attachment collar 11 having a pair of split collar members 13a, 13b forming a central opening 15 of sufficient diameter so as to accommodate IV poles having a range of diameters as may be conventional for a wide variety of commercially available IV pole stands of different manufacturers. The split collar members 13a, 13b are hingedly connected at their back ends to form a closed split, as indicated at 17, and have an openable split 19 at the front of collar 11 generally opposite the closed split. A spring 21 biases the split collars 13a, 13b to a closed position in which the split collars fit around the IV pole 3 and in which the openable split 19 is effectively closed, thus securely mounting the stop device on pole 3 when the pole is captured within the central opening 15. A spring arm 23 is cantilevered to extend out from one of the split collars (e.g., split collar 13b) and a stop or brake pad, as indicated at 25, is carried on the distal end of the spring arm. The length of spring arm 23 is not critical so long as it has a sufficient length enabling it to be resiliently bent downwardly upon a person stepping on the stop pad such that the stop pad will frictionally engage the floor. Stop pad 25 may be in the form of a ball (as shown), a flat pad (not illustrated), or any other shape so long as it can be stepped upon by a user and so long as the stop pad frictionally engages the floor. The spring arm 23 supports the stop pad 25 in a retracted position (as shown in FIG. 2) in which the stop pad is positioned above the level of the floor on which wheels 7 rest so that the stop does not interfere with the free movement of the IV pole stand on its wheels 7. The spring arm permits movement of the stop 25 from its raised, retracted position to a stop or braking position (as shown in FIG. 2) by a nurse or other person stepping on the stop pad (as shown by foot F in FIG. 3) and forcing it into contact with the floor, thus fixing or holding the IV pole stand in place on the floor. With the IV pole stand 1 held in position relative to the floor by stepping on stop 25, the IV pole stand is firmly held on the floor in position on the floor such that it will not roll on its wheels 7 and such that the pole stand is held against falling over or tipping such that a nurse need not use one hand to hold the IV pole in position or to prevent tipping of the pole stand. In that manner, a nurse may use both hands to change an IV bag, administer a medication into the IV line, to change the setting of an IV pump supported on the IV pole, or other operation. Because the nurse or other person need not touch the IV pole 3, which may be contaminated with bacteria, the spread of disease in a hospital or other health facility may be reduced. Of course, upon the nurse releasing his or her foot from stop 25, the spring arm 23 returns the stop to its retracted position clear of the floor thus permitting the pole stand to be freely moved on its wheels 7.

Figure 4:
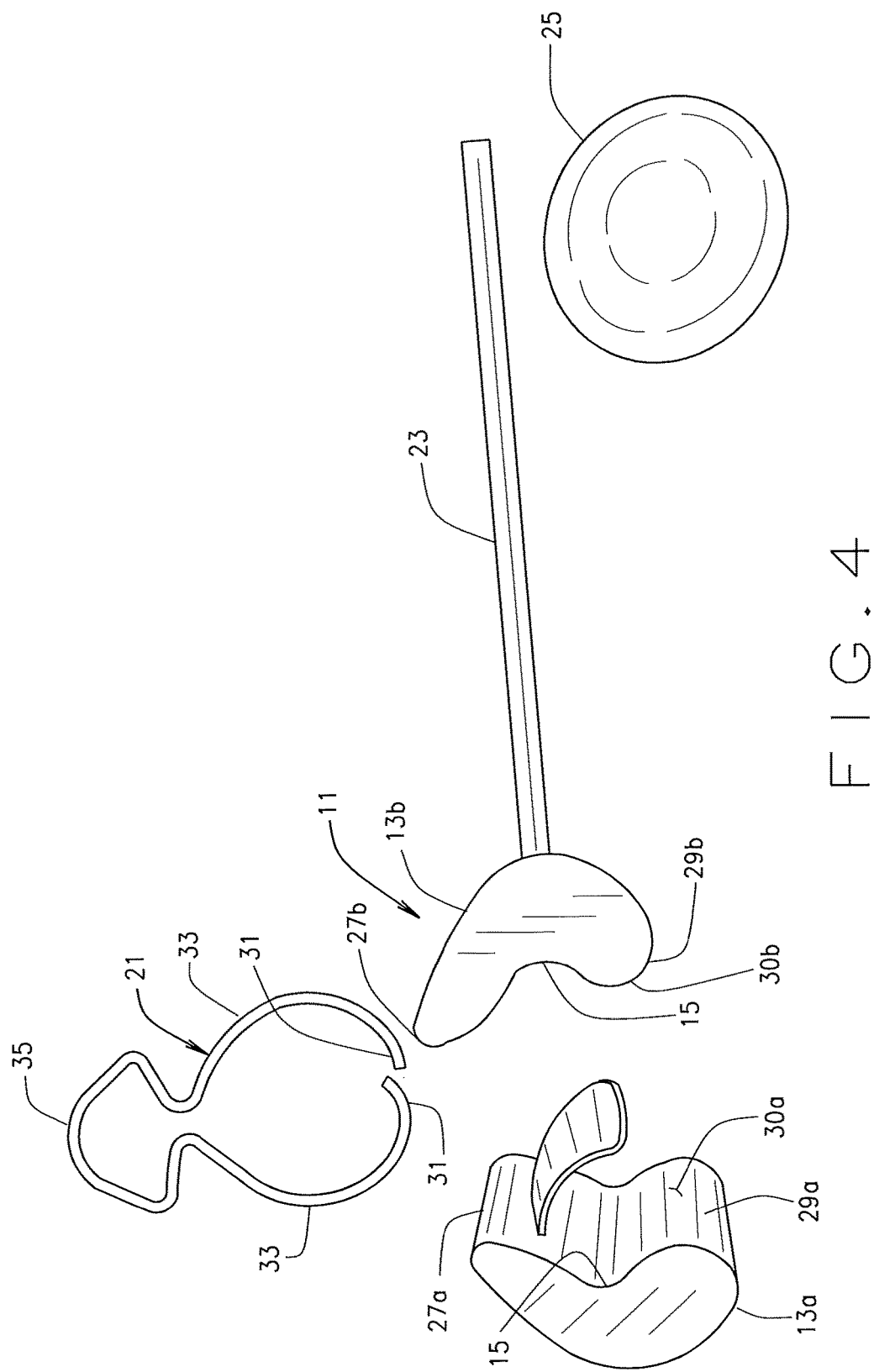
FIG. 4 is an exploded view of the primary components of an IV pole stop or brake device of the present disclosure, as shown in FIG. 3.

Referring now to FIG. 4, each split attachment collar member 13*a*, 13*b* is preferably, but not necessarily, a generally part-circular member formed of a suitable elastomer or rubber material. Each of the split members has a rear or proximate end 27*a*, 27*b*, which forms the closed split 17 when hingedly held together by spring 21. While it is preferred that the spring 21 hingedly holds the rear ends of the collar members together, it will be understood that a hinge (not shown) may be used for this purpose. Further, each of the collars members 13*a*, 13*b* members has a respective front or distal end 29*a*, 29*b* (as best shown in FIG. 4) that form the openable split 19. Preferably, the outer surface of the front ends 29*a*, 29*b* of the collar members are rounded and thus form a cam surface such that upon the front ends 29*a*, 29*b* of each of the collar members 13*a*, 13*b* being forcefully pressed against pole 3, the pole will force the open split 19 to open against the closing bias of spring 21 so that the stop 9 can be readily applied to an IV pole without the use of even simple hand tools. Once the stop 9 is so applied to an IV pole 3, the spring 21 will close the open split 19 and will thus hold the stop 9 on the IV pole. Further, the inner or rear rounded surface, as indicated at 30*a*, 30*b*, of each of the front ends 29*a*, 29*b* also form a cam surface such that when the stop device 9 is pulled from the pole, the inner surfaces force the split members 13*a*, 13*b* open so as to enable the ready removal of the stop device 9 from IV pole 3 without the use of even simple hand tools.

In FIG. 4, spring 21 is shown to be a one-piece hairpin spring formed of suitable steel spring wire or the like having hooks 31 at the forward or distal end of the spring that are adapted or configured to fit around the curved or rounded front ends 29*a*, 29*b* of each of the collar members 13*a*, 13*b* so as to hold the spring relative to the collar members. Alternatively, each of the hooks 31 may be inserted into a respective opening (not shown) in each of the collar members to hold the spring in place. Each side of spring 21 further has a part circular portion 33 extending rearwardly from each of the hooks 31 and formed to lie on the outside of each of the collar members. Each of the collar members 13*a*, 13*b* may have a groove (not shown) formed in the outer surface thereof for receiving a corresponding part-circular portion 33 of the spring 21. The rear ends of the part circular portions 33 of the spring are joined by a hairpin spring portion 35, which biases the part circular portions 33 and the hooks 31 inwardly so as to resiliently hold the split attachment collar 11 closed thereby holding the IV pole stand stop 9 in position on IV pole 3, and which hingedly joins the rear ends of the collar members to form the closed split 17. Spring 21 has sufficient force to hold the split collar members in their closed positions thus resiliently holding the openable split 19 closed. Those of ordinary skill in the art will recognize that while the hairpin spring 21 may be preferred, springs of other types may be used in accordance with the present disclosure to bias the collar members in their closed positions.

It will be appreciated that because central opening 15 is sufficiently large so as to receive poles 3 of various diameters, the collar or attachment device is loosely held on the pole such that it may rotate on the pole. If upon use, the stop pad is positioned above a leg 5, the nurse or other person may readily rotate the stop device on the pole with their foot such that the stop pad 25 is clear of a leg so that it may be pressed down to frictionally engage the floor.

As best shown in FIGS. 3 and 4, spring arm 23 is an elongated member of suitable spring material (e.g., spring steel) so as to cantilever extend in a generally horizontal direction outwardly from attachment collar 11 when the collar is attached to an IV pole 3 a distance that is preferably somewhat less than the radial spacing of the wheels 7 from pole 3. The spring arm 23 is securely attached to its collar member 13*b*. Brake or stop pad 25 is shown to be a ball and may be preferred, but other shapes, such as a flat pad, may be used. Further stop pad 25 is preferably of a suitable rubber or elastomer material that has a relatively high coefficient of friction (e.g., about 0.3-0.8) with respect to typical hospital floors or the like. The length of spring arm 23 is such that upon a nurse or the like stepping downwardly on the stop pad, as shown in FIG. 3, the spring arm will deflect downwardly such that the bottom surface of the stop pad will be firmly pressed firmly against the floor, thus holding the IV pole stand 1 in position relative to the floor and holding the IV pole from tipping. Upon the nurse releasing the stop pad, such as by the nurse taking his or her foot off the stop pad, the spring arm 23 will resiliently return the stop pad to its retracted position clear of the floor thus allowing the IV pole stand to be freely moved on wheels 7. In this manner, a nurse may quickly hold an IV pole stand in position merely by stepping on stop pad 25 with one foot thereby freeing both hands to perform a task involving the IV pole stand and to free the IV pole stand to move on its wheels by the nurse lifting his or her foot from the stop pad. Through the use of the stop of this disclosure, it is not necessary for the nurse bend over to actuate or release a mechanical lock or brake that acts on one of the wheels 7. Further, because it is not necessary for a nurse to touch the IV pole with his or her hand to hold the pole stand in position on the floor or to steady a top-heavy IV pole stand against tipping or falling over, the risk of spreading infectious diseases that may be present on the IV pole 3 is reduced. By pressing downwardly on stop pad 25, the IV pole stand 1 is steadied against possible tipping as an IV bag is changed or upon programming an IV pump carried on the pole. It will be further appreciated that by pulling the stop device from the pole of an IV pole, the rear rounded cam surfaces 30*a*, 30*b* on collar members 13*a*, 13*b* engage the pole 3 such that pole cams open split 19 so that the stop device may be readily removed from one pole stand and applied to another IV pole stand.

Figure 5:
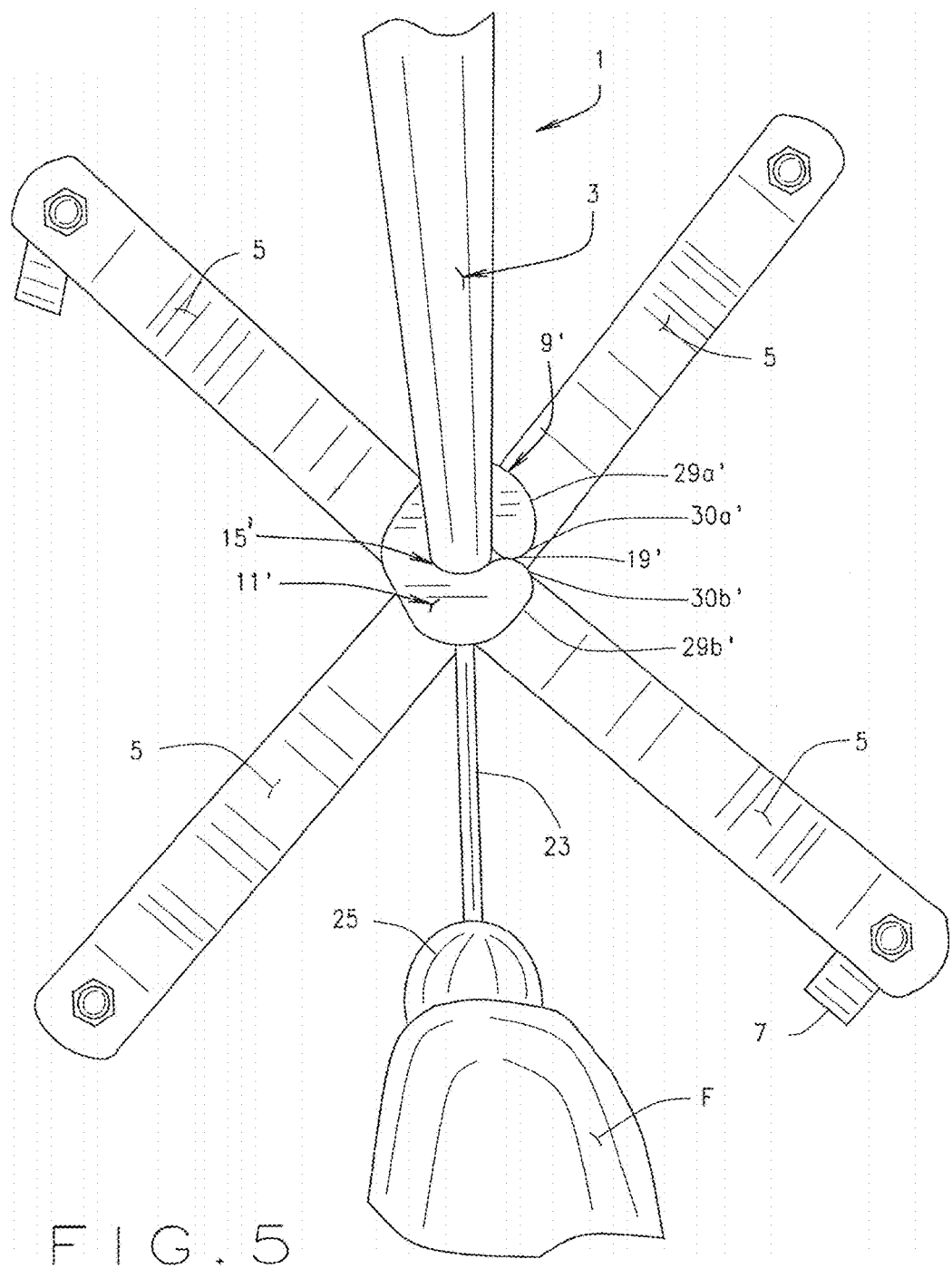
FIG. 5. Is a view similar to FIG. 3 of another preferred embodiment of the present disclosure in which the attachment collar is a unitary or one-piece collar that captures the pole in its central opening to hold the stop in place on the pole.

In another preferred embodiment of the IV pole stand brake 9', as shown in FIG. 5, instead of the attachment collar 11 having split collar members 13*a*, 13*b*, the attachment collar is to be a one-piece or unitary split collar 11' having a central opening 15' of sufficient size to accommodate a pole 3 of a variety of commercially available IV pole stands 1. Collar 11' has an openable split 19' with the ends of the collar proximate this split having rounded ends 29*a*', 29*b*' and 30*a*', 30*b*', which form cam surfaces as heretofore described. Collar 11' is preferably, but not necessarily, made of a suitable resilient plastic or elastomeric material such that when the rounded ends 29*a*', 29*b*' are forced open by the camming action of the rounded ends 29*a*', 29*b*' being forced against pole 3. With the pole received within the central opening 15', the one-piece collar 9' will resiliently bias the split 19' to a closed position such that the pole 3 is captured within the central opening. Collar 11' has the resilient spring arm 23 affixed thereto and the spring arm carries a stop pad 25 in the same manner as heretofore described. Thus, the pole stand may be firmly held in position of the floor and supported against tipping or falling over by a nurse or the like firmly stepping downwardly on stop pad 25 so that the stop pad frictionally engages the floor. When the nurse removes his or her foot from the stop pad, the spring arm 23 will return the stop pad to its retracted position thus allowing the pole stand to be readily moved on its wheels 7. Brake 9' may be removed from the pole by pulling the collar 11' away from the pole such that the rounded ends 30a', 30b' cammingly engage the pole and force open split 19' in the manner above-described.

Figure 6:
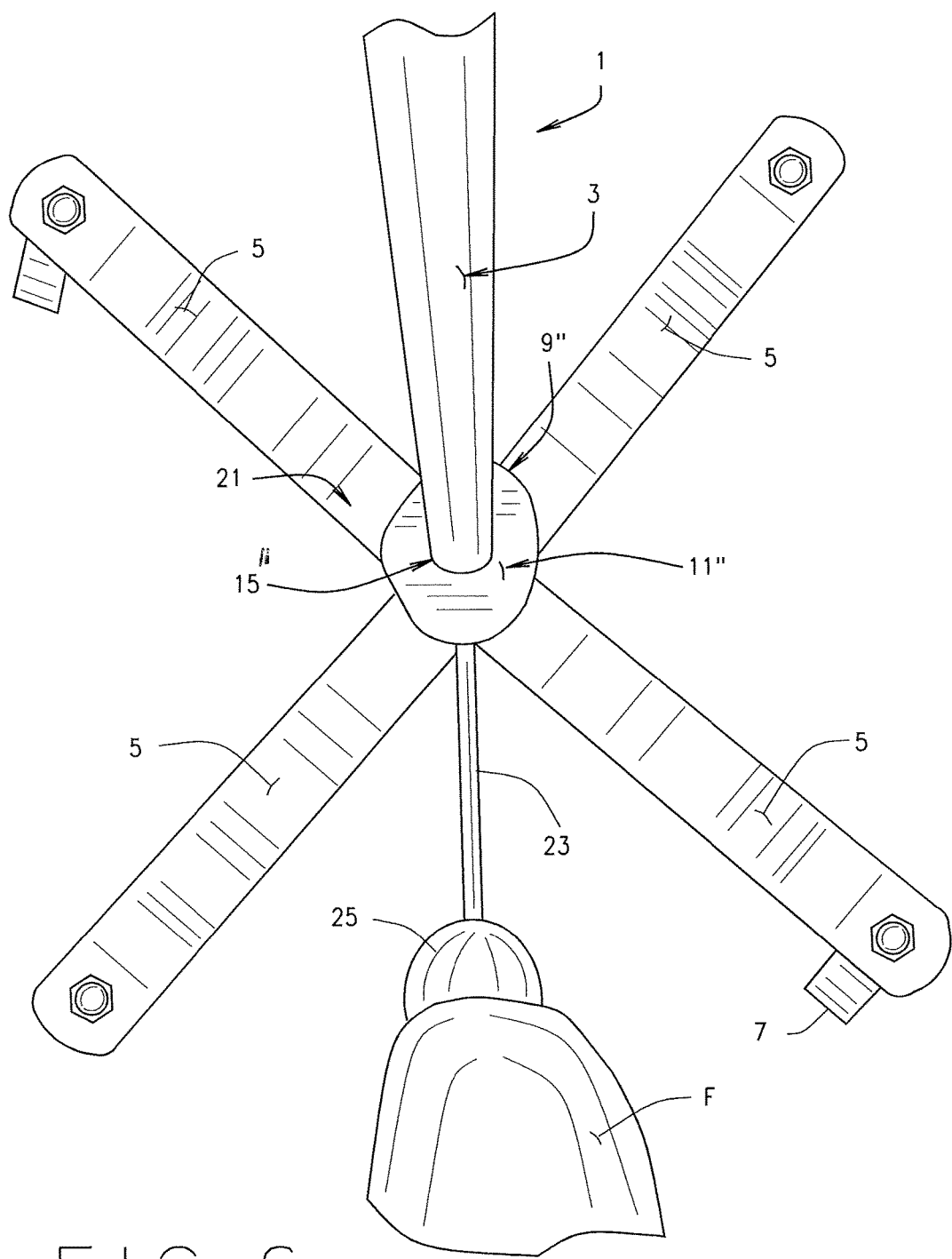
FIG. 6 is a view similar to FIG. 3 of still another preferred embodiment of the present disclosure in which the attachment collar is a solid unitary collar having a central opening for receiving the pole of the IV pole stand.
Figure 8:
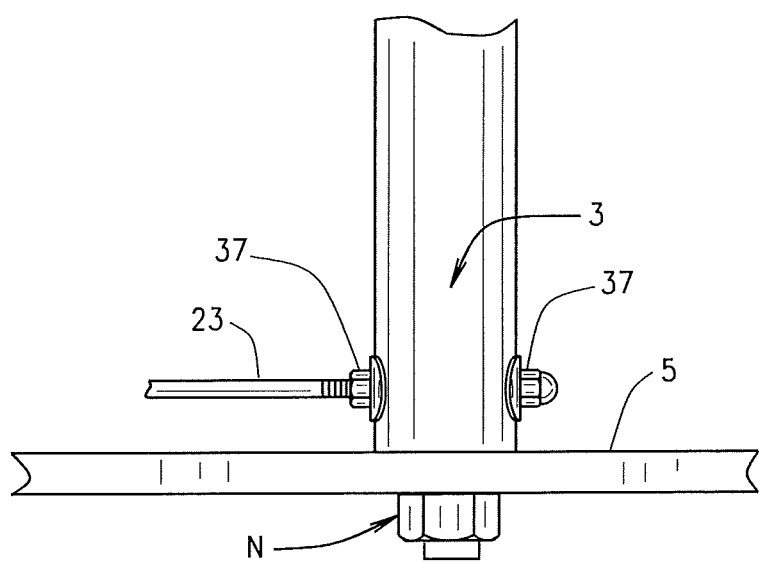
FIG. 8 is a side elevational view of a portion of an IV pole stand in which the spring arm is directly secured to the pole of the IV pole stand.

In FIG. 6, still another preferred embodiment of the IV pole stand brake 9" is shown. In this embodiment, a solid one-piece attachment collar 11" is provided that does not have an openable split, but where the collar surrounds pole 3 and captures the pole. This collar 11" may be applied to pole 3 by removing the upper extension of pole 3 and the clamp 4 from the lower portion of pole 3 and inserting the lower pole portion into the central opening 15" of the collar 11" sliding the collar down the lower portion of the pole, and then re-installing the clamp. Alternatively, collar 11" may be installed on pole 3 by removing a nut N (as shown in FIG. 8) that holds the pole on the base 5, and removing the pole from the base, inserting the pole through the central opening 15" of collar 11" and re-installing the pole on the base. Like attachment collars 11 and 11', collar 11" has a spring arm 23 affixed to it and the spring arm will carry stop pad 25 in the same manner as the other embodiments above described. Of course, this third embodiment will operate in the same manner as the other embodiments.

Figure 7:
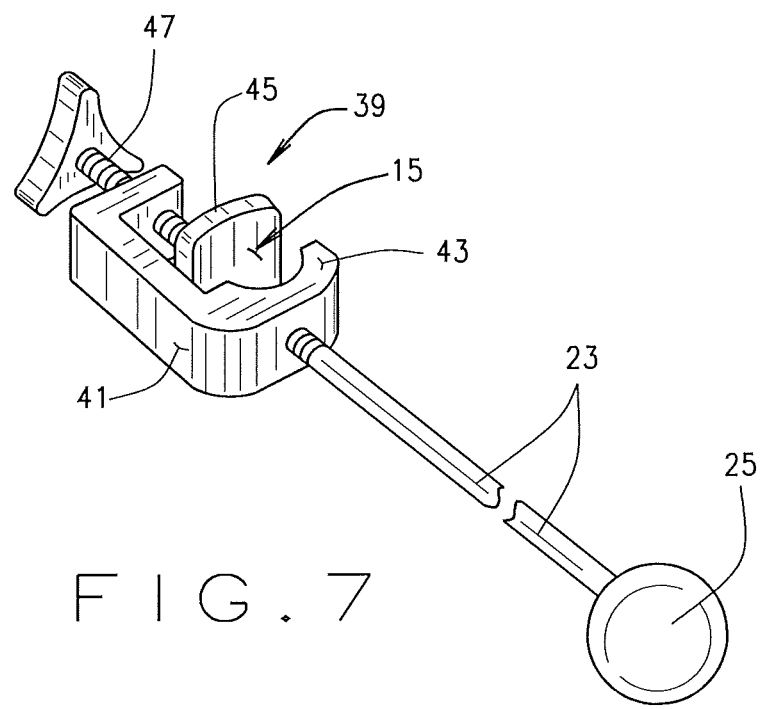
FIG. 7 is a perspective view of a C-clamp attachment device that may be used to removably secure or attach the spring arm and the stop pad to the pole of an IV pole stand.

Referring now to FIG. 7, a C-clamp-type attachment device, as indicated at 39, may be used to removably attach spring arm 23 and stop pad 25 to the pole 3 of any commercially available IV pole stand 1. This C-clamp 39 has a clamp body 41 having a curved fixed jaw 43. The C-clamp further has a movable jaw 45 carried on an adjustment or clamp screw 47. The fixed and movable jaws form opening 15 for receiving pole 3 therebetween such that poles of various diameters may be received and clamped between the jaws. In order to install the IV pole brake of the present disclosure to the pole of virtually any commercially available IV pole stand using the C-clamp attachment device 39, the movable jaw 45 is opened a sufficient distance such that pole 3 can be received between the jaws 43 and 45 of the C-clamp. Then, adjustment or clamp screw 47 is tightened so that the pole is firmly clamped between the jaws of the C-clamp so as to attach spring arm 23 to pole 3. In this manner, the C-clamp is adjusted such that the spring arm will extend out from and be cantilever supported from the pole and such that stop pad 25 is clear of a leg of base 5 so that upon a nurse stepping on stop pad 25, the spring arm 23 will deflect downwardly and the stop pad can frictionally engage the floor and thus hold the IV pole stand against movement on the floor and against tipping or falling over while a nurse or the like performs operations on an IV bag supported on the pole stand or adjusts an IV pump supported on the pole 3. Of course, upon the nurse or user removing his or her foot from the stop pad, the spring arm will resiliently return the stop pad to its retracted position clear of the floor such that the IV pole stand is free to move on its wheels 7.

As shown in FIG. 8, in its simplest form, the stand brake of the present disclosure could be manufactured to be a part of the IV pole stand by the manufacturer of the pole stand. In such instances, an attachment collar 11 would not be needed. Instead, the spring arm 23 may be affixed directly to the pole 3 just above the base 5 and the spring arm would carry the stop pad 25 in the manner as above described. As shown in FIG. 8, one end of the spring arm 23 is received in holes in pole 3 just above the level of base 5. Nuts N secure the spring arm to pole 3, thus eliminating the need for an attachment collar or the like. To operate this embodiment, a nurse or the like would merely step on the stop pad in the manner heretofore described such that the stop pad can frictionally engage the floor so as to hold the pole stand from moving on wheels 7 and to hold the pole stand from tipping. Of course, upon releasing one's foot from the stop pad, the spring arm would return the stop pad to its retracted position.

It will be understood that the various attachment devices, as illustrated in FIGS. 2-8, constitute means for attaching or affixing spring arm 23 and stop pad 25 carried thereby to the pole 3 of an IV pole stand 1.

As various changes could be made in the above constructions without departing from the broad scope of the disclosure, it is intended that all matter contained in the above description or shown in the accompanying drawings shall be interpreted as illustrative and not in a limiting sense.

What is claimed is:

1. A stop for an IV pole stand having a base mounted on a plurality of wheels and having a pole extending vertically from said base, said stop comprising an attachment member having a central opening adapted to receive said pole, and a stop pad supported on a spring arm cantilevered from said attachment member such that upon said stop pad being stepped on by a person, said spring arm can resiliently deflect downwardly such that said stop pad can be pressed against the floor to hold the pole stand in place on the floor and to resist tipping of the pole stand, wherein said attachment member is a collar comprised of a pair of collar members, a spring for holding said collar members in a closed position such that with said pole received within said central opening said collar members can substantially surround said pole, each of said collar members having a front end and a rear end, the front ends of said collar members being biased to a closed position by said spring, the front ends of said collar members each having a cam surface configured such that upon the front ends of said collar members being forcefully pressed against said pole said cam surfaces can force the front ends of said collar members apart so that said pole can pass therebetween to be received in said central opening and so that when said pole is received in said central opening said spring can resiliently close said collar members, and said stop pad supported on said spring arm cantilevered from one of said collar members such that upon said stop pad being stepped on by the person, said spring arm will resiliently deflect downwardly and said stop pad can be pressed against the floor to hold the pole stand in place on the floor and to resist tipping of the pole stand.

2. The stop for an IV pole stand as set forth in claim 1 wherein said collar members are of a suitable elastomeric material.

3. The stop for an IV pole stand as set forth in claim 1 wherein said spring arm is of a suitable resilient material so that it can be readily deflected downwardly upon being stepped upon such that said stop pad frictionally engages the floor to hold the IV pole stand in place and so that upon the person removing his or her foot from the stop page said spring arm can resiliently return the stop pad to a retracted position clear of the floor.

4. The stop for an IV pole stand as set forth in claim 3 wherein said stop pad is of a material that has a sufficiently high coefficient of friction such that when it is pressed against the floor, the IV pole stand can be held in place on the floor and against tipping.

5. The stop for an IV pole stand as set forth in claim 4 wherein said stop pad has a coefficient of friction with the floor ranging between about 0.3 and about 0.8.

6. The stop for an IV pole stand as set forth in claim 1 wherein said spring is a hairpin spring having a pair of distal ends with each distal end engaging a respective one of said collar members proximate the distal or front end of its respective collar member, said spring further having a curved portion adapted to be on the outside of its respective collar member and a hairpin spring portion opposite said front ends of said collar members.

\* \* \* \* \*